United States Patent
Baer et al.

(10) Patent No.: US 9,805,612 B2
(45) Date of Patent: Oct. 31, 2017

(54) INTEREST-ATTENTION FEEDBACK METHOD FOR SEPARATING COGNITIVE AWARENESS INTO DIFFERENT LEFT AND RIGHT SENSOR DISPLAYS

(75) Inventors: Nikolaus Baer, Belmont, CA (US); Wolfgang Baer, Mountain View, CA (US)

(73) Assignee: Nascent Systems, Inc., Carmel Valley, CA (US)

( * ) Notice: Subject to any disclaimer, the term of this patent is extended or adjusted under 35 U.S.C. 154(b) by 956 days.

(21) Appl. No.: 13/455,134

(22) Filed: Apr. 25, 2012

(65) Prior Publication Data

US 2012/0282585 A1    Nov. 8, 2012

Related U.S. Application Data

(60) Provisional application No. 61/518,365, filed on May 4, 2011.

(51) Int. Cl.
| | | |
|---|---|---|
| *G09B 5/00* | (2006.01) | |
| *G09B 5/06* | (2006.01) | |
| *G09B 19/00* | (2006.01) | |
| *A61B 3/08* | (2006.01) | |
| *H04N 13/04* | (2006.01) | |

(52) U.S. Cl.
CPC ............ *G09B 5/067* (2013.01); *G09B 19/00* (2013.01); *A61B 3/08* (2013.01); *H04N 13/0436* (2013.01)

(58) Field of Classification Search
CPC ............................... A61B 3/08; H04N 13/0436
USPC ......................................................... 351/200
See application file for complete search history.

(56) References Cited

U.S. PATENT DOCUMENTS

| | | |
|---|---|---|
| 3,760,181 A | 9/1973 | Daly et al. |
| 4,439,157 A | 3/1984 | Breglia et al. |
| 4,632,501 A | 12/1986 | Glynn |
| 4,636,866 A | 1/1987 | Hattori |
| 4,655,543 A | 4/1987 | Montagu |
| 4,861,125 A | 8/1989 | Vaught |
| 4,902,893 A | 2/1990 | Burrer |
| 5,009,473 A | 4/1991 | Hunter et al. |
| 5,233,458 A * | 8/1993 | Moffitt .................. G02B 23/18 351/201 |
| 5,334,991 A | 8/1994 | Wells |

(Continued)

*Primary Examiner* — Michael C Stout
*Assistant Examiner* — Patrick Fernandes

(57) ABSTRACT

A method for using an interest-attention feedback loop involving the determination of the interest of a person in a left sensor stimulation stream and a right sensor stimulation stream, and the adjustment of attention factors to balance that interest, with the intent to facilitate, or train, a person to intentionally suppress binocular fusion and operate within the dual experience, where the person is able to simultaneously render separate left and right mental displays. The dual experience allows the person new mental processing capabilities that can produce novel information synthesis, double the information input in man machine interfaces, and allow reaction to the cognitive awareness of two simultaneous world views. This includes facilitating awareness and interactions with two different computer screen interfaces simultaneously, reducing fatigue associated with optical screen switching, and encouraging the fusion of two different simultaneous experiences into an abstract information synthesis.

14 Claims, 7 Drawing Sheets

(56) References Cited

U.S. PATENT DOCUMENTS

| | | | | |
|---|---|---|---|---|
| 7,290,878 B1* | 11/2007 | Hofeldt | ............... | A61B 3/08 |
| | | | | 351/200 |
| 7,946,707 B1* | 5/2011 | McDonald, II | ........ | A61B 3/032 |
| | | | | 351/203 |
| 2003/0032894 A1* | 2/2003 | Hu | ................. | A61B 5/04842 |
| | | | | 600/558 |
| 2007/0200927 A1* | 8/2007 | Krenik | ............... | A61B 3/032 |
| | | | | 348/47 |
| 2008/0269629 A1* | 10/2008 | Reiner | ............. | A61B 5/4836 |
| | | | | 600/544 |
| 2009/0115966 A1* | 5/2009 | Waldorf | ............ | A61B 3/112 |
| | | | | 351/210 |
| 2012/0069296 A1* | 3/2012 | Li et al. | .................... | 351/201 |

\* cited by examiner

FIG. 1 --PRIOR ART--

INTEREST-ATTENTION FEEDBACK METHOD FOR SEPARATING COGNITIVE AWARENESS INTO DIFFERENT LEFT AND RIGHT SENSOR DISPLAYS

CROSS-REFERENCE TO RELATED APPLICATIONS

Provisional Patent Application No. 61/518,365 date May 4, 2011, "Interest Attention Feedback for Simultaneous Visualization of Different Left and Right Eye images"

FEDERALLY SPONSORED RESEARCH

One of the inventors, Wolfgang Baer, was employed by the Department of the Navy at the Naval Postgraduate School. He has worked with Helmet mounted displays systems in the course of his normal duties. The attention control feedback method was not discovered, invented, or sponsored by federally funded research.

SEQUENCE LISTING

Not Applicable

BACKGROUND OF INVENTION

Technical Field

This invention relates to the simultaneous rendering of separate left and right mental displays by a person, and more specifically, to a device for training a person to simultaneously render separate left and right mental displays.

Prior Art

The brain of a person normally renders one coherent three-dimensional mental display by fusing an image presented to the left eye and an image presented to the right eye of the person, in a process that is often referred to as binocular fusion or binocular combination. The image presented to the left eye and the image presented to the right eye are typically highly related and only offset by the distance between the two eyes, because both images typically come from a single scene. Even when presented with separate images to each eye, the brain of a person typically continues to perform binocular fusion in an attempt to render one coherent three-dimensional mental display.

The terms "dichoptic" and "dichoptic presentation" are used to identify the presentation of separate images to each eye. Dichoptic vision systems are typically designed to provide simultaneous narrow and wide field of view images to overcome the resolution limitations of computer displays. Dichoptic vision systems employ dual eye input to augment and enhance stereo vision by increasing the fovea information density in one eye, but do not address useful alternatives to binocular fusion.

The term "binocular rivalry" is used to describe a mental effect caused by dichoptic presentations. Binocular rivalry is caused as the brain of a person attempts to perform binocular fusion and render one coherent three-dimensional image by continually switching between rendering a first three-dimensional image based only on the information presented to the right eye, and then subsequently rendering a second three-dimensional image based only on information presented to the left eye.

Binocular fusion, dichoptic presentation and binocular rivalry have been extensively studied and helmet mounted displays, optical glasses, and periscope devices that allow dichoptic presentation and the management of binocular rivalry and binocular fusion abound. For example, U.S. Pat. No. 5,334,991 by Wells et al. and published Aug. 2, 1944 shows head mounted mirror arrangements that allow two separate images to be introduced to the left and right eye. Related patent documents showing similar but different mounting configurations are cited as follows.

| U.S. PATENT DOCUMENTS | | | |
| --- | --- | --- | --- |
| 3,760,181 | August 1973 | Daly et al. | 250/332 |
| 4,439,157 | March 1984 | Breglia et al. | 434/40 |
| 4,457,580 | July 1984 | Klose | 359/221 |
| 4,632,501 | December 1986 | Glynn | 359/199 |
| 4,636,866 | January 1987 | Hattori | 358/236 |
| 4,655,543 | April 1987 | Montagu | 359/214 |
| 4,861,125 | August 1989 | Vaught | 359/214 |
| 4,902,893 | February 1990 | Burrer | 359/201 |
| 5,009,473 | April 1991 | Hunter et al. | 359/214 |

While mirror devices for displaying images to the left eye and right eye have been patented, such devices are designed for binocular fusion applications. US patent application number 20090225001 A1 by Biocca et. al. and published Sep. 10, 2009 shows a hybrid system designed to project computer controlled wide field of view into one eye and a second narrow field of view onto a patented dome device. The system increases the apparent resolution of a fovea view and a peripheral view from two images of differing zoom on the same scene. A small business innovative research grant (SBIR) was discovered using a similar setup designated as a Dichoptic Vision System(DIVS) under contract FA8650-10-M-6068 with performance dates (Apr. 22, 2010 to Jan. 21, 2011) with principle investigator Dale R. Tyczka. Again, this system was explicitly designed to allow merging of narrow and wide field of view using two computer controlled cameras.

Similarly, U.S. Pat. No. 8,328,354 by Li, et. al. and published on Dec. 11, 2012 teaches a system and method to use dichoptic presentation to diagnosis and treat binocular vision disorders, by adjusting images presented the left and right eye to train a person with a binocular vision disorder to correctly perform binocular fusion and render one coherent three-dimensional mental display. Again, the dichoptic presentation is used to train a person to perform binocular fusion.

The current state of the art can be summarized as shown in FIG. 1 (Prior Art), where during a process of binocular fusion 100 a person sees a left image 110 and a distinct right image 120 and the brain 150 of the person renders a coherent three-dimensional display 130. It is understood, in the prior art, that the coherent three-dimensional display 130 may be produced by the brain 150 through binocular fusion or binocular rivalry. Note also, that a person may also render a version of the one coherent three-dimensional display 130 from only the left image 110 presented to the left eye or the right image 120 presented to the right eye, as encountered in normal vision when one eye is closed.

Failure of the brain to render a coherent three-dimensional display 130, is considered a binocular vision disorder in the prior art. While dichoptic presentation, binocular fusion, and binocular rivalry have been extensively studied and dichoptic vision systems exist, such research and devices have been developed upon the paradigm of a person performing, or attempting to perform, binocular fusion 100 to render one coherent three-dimensional display 130.

This ability to render one coherent three-dimensional display 130 is important in the natural world, but in the current information age there is an increased need for people to process more information simultaneously. Despite the need for people to be able to process more information simultaneously, there has been no research or development under the paradigm of a person intentionally suppressing binocular fusion 100, so as to simultaneously render separate left and right mental displays. Therefore, what is needed in the art is an approach to facilitate, or train, a person to intentionally suppress binocular fusion 100, so as to simultaneously render separate left and right mental displays.

SUMMARY OF INVENTION

The inventors have discovered that a person is capable of simultaneously rendering mental displays that are substantially different from the one coherent three-dimensional display 130 and may deliver benefits in the current information age. Specifically, separate left and right mental displays are substantially different from the one coherent three-dimensional display 130 produced by binocular fusion, but may allow a person to process more information simultaneously.

This patent application is based upon experiments conducted with dual eye display systems constructed at Nascent Systems Incorporated that were designed to explore the possibility of expanding human cognitive bandwidth by using one eye per computer screen rather than both eyes per single computer screen. Individual left and right computer driven displays and mirror setups were tested.

As discussed, it was previously known that the vision system of a person could operate in two distinct modes: binocular fusion 100 or binocular rivalry. However, the experiments conducted by Nascent Systems Incorporated revealed that the vision system of a person could operate in a third distinct mode, where a person suppresses binocular fusion 100, so as to render separate left and right mental displays. The inventors define this third mode as the "dual experience." During the dual experience mode, the separate left and right mental displays are simultaneously apparent to the person and the person can therefore process and act on information from both the left and right mental display simultaneously. The initial effect of dual experience mode, is that the two left and right images can appear as though separately projected on surfaces surrounding the person.

The invention described in this Patent Application pertains to a method for using an interest-attention feedback loop involving the measurement of the interest of a person in a left sensor stimulation stream and a separate right sensor stimulation stream, and the adjustment of attention factors, or stimulations, to balance that interest, with the intent to facilitate, or train, a person to intentionally suppress binocular fusion 100, so as to simultaneously render separate left and right mental displays. That is, to facilitate, or train, the person to operate within the dual experience previously described. To train a person to simultaneously render separate left and right mental displays requires measurement and feedback control of attention factors, which make the left mental display more or less interesting than the right display.

The purpose of this invention is, (1) define an interest-attention feedback loop for controlling the attention to a left sensor stimulation stream and a separate right sensor stimulation stream in order to facilitate, or train, a person to intentionally suppress binocular fusion, so as to simultaneously render separate left and right mental displays, (2) to define a method for training a person to intentionally suppress binocular fusion, so as to simultaneously render separate left and right mental displays, (3) to train the person to understand and respond to the separate left and right mental displays.

Various embodiments of this invention may utilize various sensor stimulation streams, such as, but not limited to, visual images or sequences of visual images transmitted to the eyes of the person that can collectively be referred to as optic stimulations patterns. Other embodiments include audio signals transmitted to the ears of the person or tactile sensations transmitted to the skin of the person. Embodiments of this invention would then determine and apply adjustment to the attention factors in these additional sensor stimulation streams. A person skilled in the art would understand that these are example adjustments to attention factors of example sensor stimulation streams, and other adjustments, attention factors, and sensor stimulation streams that facilitate the dual experience in a person are included in the scope of this patent.

Various embodiments of this invention may include one-or-more advantages over other embodiments. However, since treatment of faulty binocular fusion has only been done as a medical corrective procedure that strengthens lazy-eye muscles to re-establish binocular fusion and does not reprogram the optic data processing in the brain or provide an enhancement of optical capabilities, the relative advantages are between alternative embodiments of our method and not between our embodiments and forgoing inventions.

The forgoing has broadly outlined the features and advantages of the invention in order that the following detailed descriptions of its operation tied to specific example embodiments can be better understood in the context of the interest-attention feedback loop and the dual experience specified in this application. The following sections provide further details of the novel features and operation of the invention. These features will be better understood when considered in connection with the accompanying drawings.

Advantages of Invention

This invention allows a person to process more information simultaneously, by becoming aware of, understanding, and reacting to two different sensor stimulation streams simultaneously. For example, allowing a person to be simultaneously aware of, understand, and interact with a left image and a distinct right image. This invention could, in effect, double the cognitive bandwidth of a person by facilitating the person's ability to utilizing distinct images, i.e. two distinct computer screens, simultaneously, rather than using two eyes for a single image. It could also allow the merging of two separate input data sources into more abstract synthesis of situational awareness than the three-dimensional world presentation conventionally produced by a human operator.

The potential benefits and utility of dual experience operation are numerous and a partial list of advantages and new applications includes:
  a) Fatigue reduction: Simultaneous image awareness and information extraction by internal mental operation is less fatiguing than utilizing explicit eye movement between different images.
  b) Cognitive bandwidth enhancement: The human operator is able to maintain, utilize and react to different information presented to the left and right eye without switching between versions of the one coherent three-dimensional mental display 130 and thus avoid the time share overhead of the current mental processing.

c) Alternative vision synthesis: We know the human processing system render one coherent three-dimensional mental display 130 of the world from two images. We now know the brain can also synthesize alternative information presentation displays when different inputs are presented. Examples for differences in image inputs that lead to novel synthesis are:
different time sequences
left image and a right image generate a 360 degree scenes
inside/outside views of complex objects
synthesis of abstract planar information displays
alternatives selection and evaluation d) Attention measurement: We know left and right eye inputs will be selected by the brain in response to attention factors such as illumination, image movement, or image changes, or intrinsic interest in image content. The difference in attention factors between left and right eye input measures the interest of the person in the left image and right image. Such measurements can be used for design of:
man machine interfaces
warning messages
attention value measurement of image content design e) Augmented reality and image registration: Immediately useful applications for dual experience involves the use of live and synthetically generated images for the left and right eye during, for example, unmanned aerial vehicle flights.

SUMMARY OF DRAWINGS

For a more complete understanding of our invention, reference is now made to the following description of selected embodiments of the Attention Feedback Method in conjunction with the accompanying drawings.

DETAILED DESCRIPTION OF DRAWINGS

Figure 1:
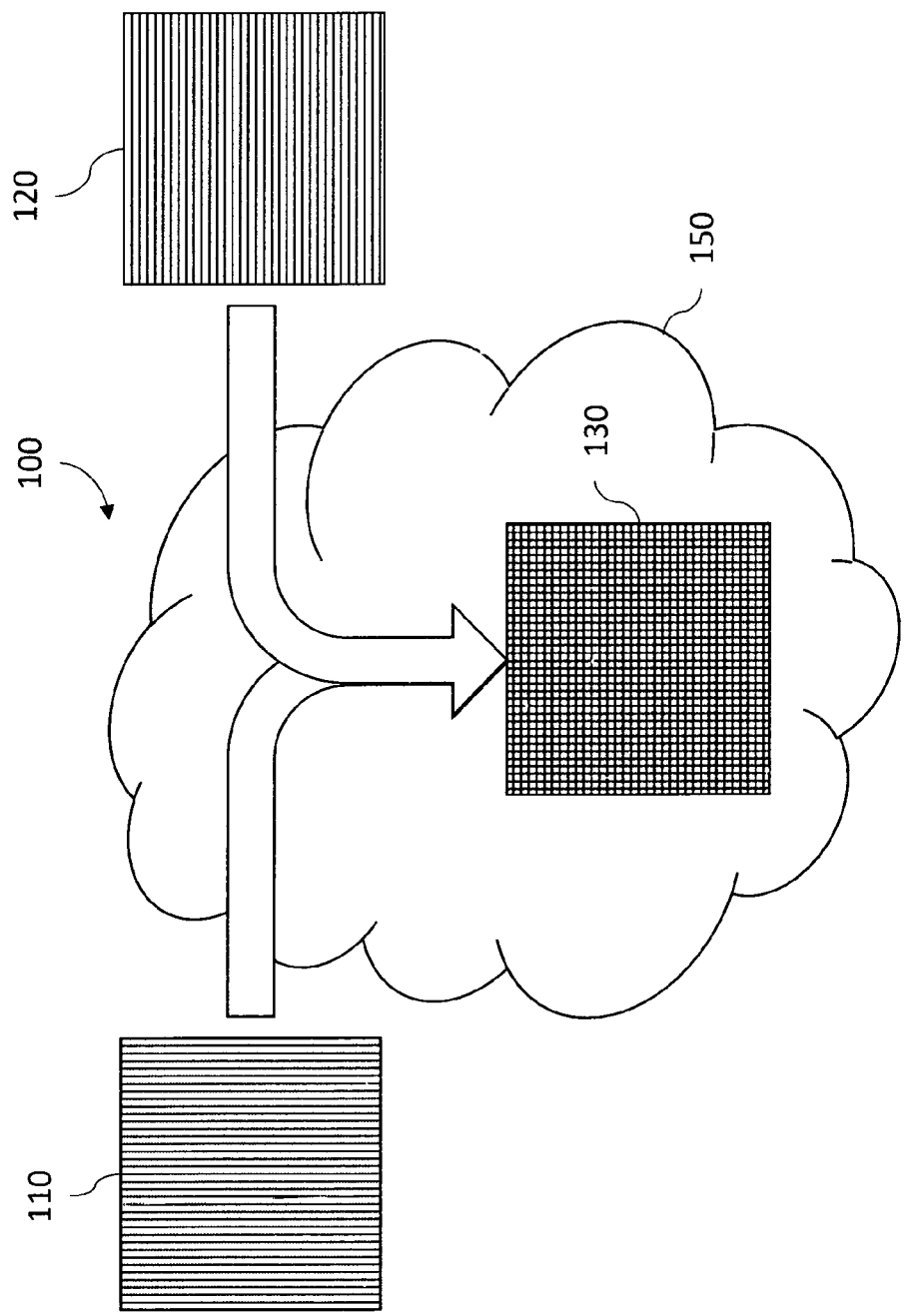
FIG. 1 (Prior Art) illustrates the prior art understanding of binary fusion in the brain of a person.
Figure 2:
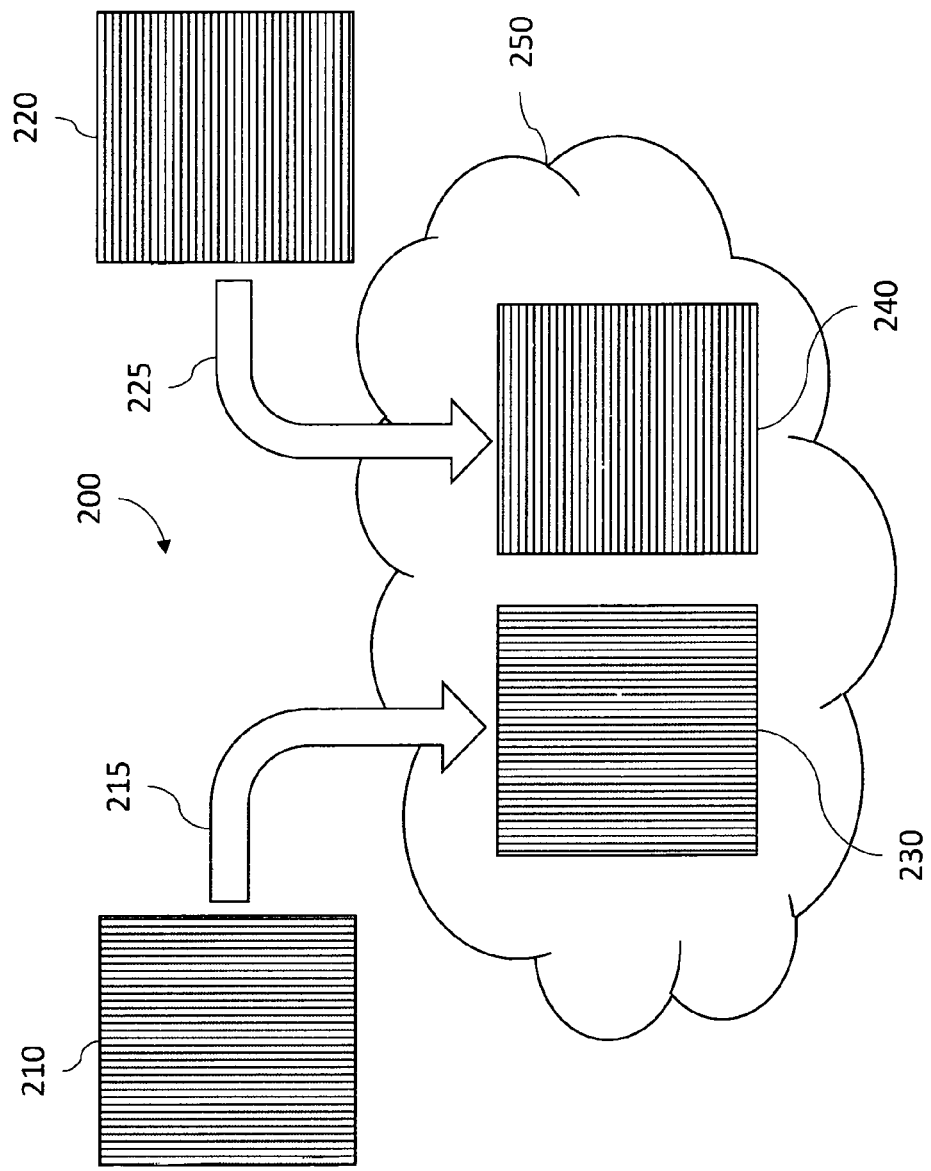
FIG. 2 illustrates the dual experience with a left image as the left sensor stimulation stream and a right image as the right sensor stimulation stream.

FIG. 2 illustrates the dual experience 200 with a left image as the left sensor stimulation stream and a right image as the right sensor stimulation stream. A left image 210 is presented to a person as the left sensor stimulation stream 215 while a right image 220 is also presented to the person as the right sensor stimulation stream 225. The brain 250 of the person then renders a separate left mental display 230 and right mental display 240. In the dual experience 200, the person renders and can interact with the left mental display 230 and the right mental display 240 separately and simultaneously. This is wholly different to the person rendering, or being trained to render, one coherent three-dimensional display 130 as in the prior art understanding of binocular fusion 100.

To suppress binocular fusion 100 and maintain the rendering of separate left mental display 230 and right mental display 240 the attention factors that make the left image 210 or the right image 220 more interesting must be balanced. Balancing the attention factors, represses the brains tendency to select the left image 210 or the right image 220 for rendering one coherent three-dimensional display 130.

In various embodiments, the attention factors include but are not limited to:
1) image, audio, or tactile changes in illumination, volume, or pressure respectively
2) image, audio, or tactile changes in content such as color, texture, or rhythm
3) image, audio, or tactile changes in content motion, image size, or angular aspect.
4) Any surprises or unanticipated changes of the above listed attention factors.

The identification of attention factors and ability to control such attention factors in both the left and right input sensor sets, the senses on the left side or right side of the body, is not enough to assure dual experience 200 for a person. To achieve dual experience 200, it is necessary to determine the interest of the person in the left sensor stimulation stream 215 and the right sensor stimulation stream 225 and adjust the application of attention factors to balance this interest. Hence, an interest-attention feedback loop must be established to continually balance this interest by adjusting the attention factors based on the interest of the person in the left sensor stimulation 215 and the right sensor stimulation stream 225. For example, if the person becomes more interested in the left sensor stimulation stream 215 than the right sensor stimulation stream 225, then the right image 220 could be more strongly illuminated to balance the interest of the person in both the left sensor stimulation stream 215 and the right sensor stimulation stream 225 and maintain the dual experience 200 for the person.

It was also found that balancing the attention factors further involves controlling attention factors in the environment surrounding the person. If the person becomes distracted by attention factors in the environment surrounding the person, then the dual experience 200 may not be achieved. As such, the left image 210 and the right image 220 should be presented in such a way as to block or mitigate attention factors in the environment surrounding the person.

Figure 3:
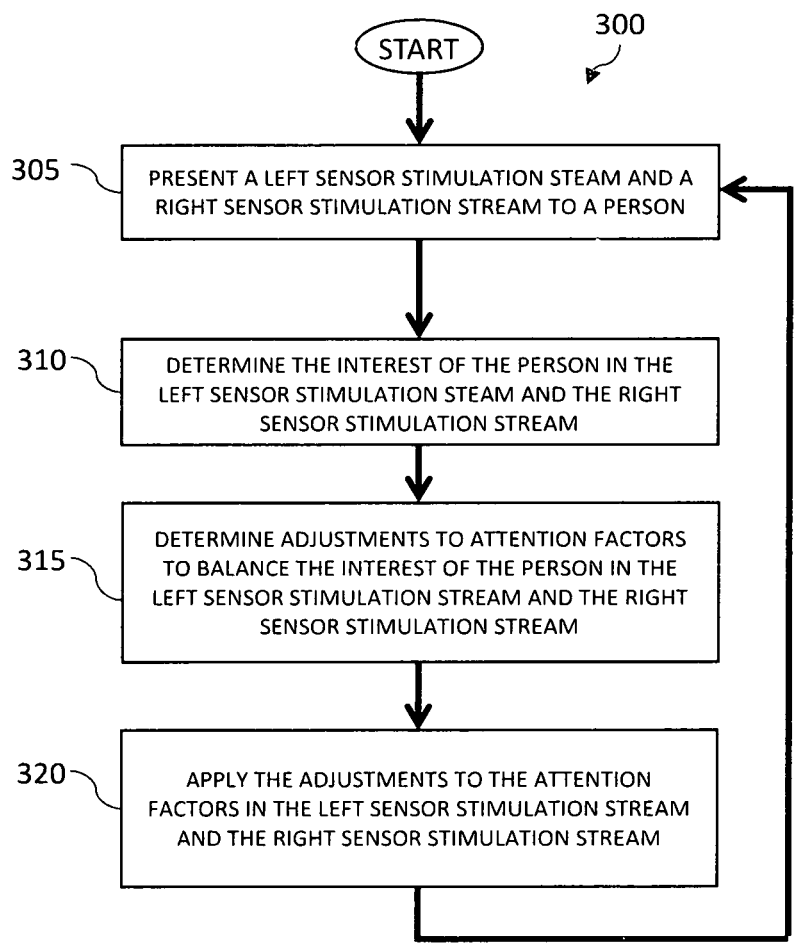
FIG. 3 illustrates a method for the interest-attention feedback loop.

FIG. 3 illustrates the interest-attention feedback loop 300, according to one embodiment. The steps of the interest-attention feedback loop 300 are described as being performed by a system, such as the systems described below in FIG. 4, FIG. 5, FIG. 6, and FIG. 7, but a person skilled in the art would understand that these are example embodiments and any system to perform the steps of the interest-attention feedback loop 300 is included in the scope of this patent. The interest-attention feedback loop 300 includes the real-time execution of the following steps. The interest-attention feedback loop 300 begins at step 305, where a system presents the left sensor stimulation stream 215 and the right sensor stimulation stream 225 to a person. The left sensor stimulation stream 215 may be, for example, the left image 210 presented to the left eye and the right sensor stimulation stream 225 may be, for example, the right image 220 presented to the right eye.

In other embodiments, presenting the left sensor stimulation stream 215 and the right sensor stimulation stream 225 to a person may include generating images, sounds, or tactile sensations, which are presented to the person.

At step 310, the system determines the interest of the person in the left sensor stimulation stream 215 and the right sensor stimulation stream 225. As shown below in conjunction with various embodiments of the system. The embodiments generally fall into two categories, those in which the person voluntarily participates in the determination of step 310 and those were a computer performs step 310 by measuring the state of the person. The person may monitor his or her own interest in the left sensor stimulation stream 215 and the right sensor stimulation stream 225 and voluntarily perform some action, such as moving a lever, joystick, dial, mouse, pressure sensor, potentiometer, or body part, from which the system determines that interest. In the above examples, the person could perform the movements with a hand, foot, head, arm, or other suitable body part. The advantages to systems that include voluntary determination of interest are lower cost and ease of use. Such implementations are appropriate for low cost introductory kits that make a person familiar with the notion of the dual experience 200.

In other embodiments, the system may determine a quantifiable measurement of this interest by measuring involuntary changes in the state of the person, such as involuntary eye movements or brain activity measured by an electro-encephalogram. The advantages of systems that include measurements of involuntary changes in the state of the person may be well suited for allowing the person to manually operate machinery such as an unmanned aerial vehicle.

At step 315, the system determines adjustments to the attention factors to balance the interest of the person in the left sensor stimulation stream 215 and the right sensor stimulation stream 225, thus facilitating the dual experience 200. In some embodiments, the system may determine a mechanical adjustment of a light source to change the brightness of the left image 210 or right image 220. In other embodiments, the system may determine the adjustment by selecting a modification of other characteristic of the left image 210 or right image 220, such as contrast, or movement within or of the image. In still other embodiments, the system may determine adjustments to audio signals transmitted to the ears of the person, such as volume or content of the audio signals or adjustments to the tactile sensations transmitted to the skin of the person, such as intensity of vibration or temperature.

At step 320, the system applies the adjustments to the attention factors determined in step 315 to the left sensor stimulation stream 215 and the right sensor stimulation stream 225. The system may apply the adjustments by, for example, modifying the content or brightness of the left image 210 or right image 215.

In some embodiments, the step 315 and step 320 may be combined. For example, the system may simply move a light source to the left or right to change the brightness of the left image 210 or right image 215, in response to the person voluntarily moving a lever.

The interest-attention feedback loop 300 then returns to step 315, where the left sensor stimulation stream 215 and the right sensor stimulation stream 225, with modifications from step 320, are again presented to the left eye and right eye of the person.

Through the determination of interest at step 310, determination of adjustments at step 315, and application of adjustments at step 320, the interest-attention feedback loop 300 continually updates and presents the left sensor stimulation stream 215 and a right sensor stimulation stream 225 that balance the interest of the person in the left sensor stimulation stream 215 and right sensor stimulation stream 225 and thereby facilitates the dual experience 200. Various embodiments are not limited to these exact steps in this exact order. Various embodiments may augment the steps of the interest-attention feedback loop 300 in order to suppress binocular fusion.

Initially the interest of the person may shift rapidly between the left sensor stimulation stream 215 and a right sensor stimulation stream 225, causing binocular rivalry. To prevent binocular rivalry, the interest-attention feedback loop 300 executes in real-time (or near real-time, i.e. less than the typical human response time of 100 milliseconds).

The person may feel strained, tired, nauseas, or develop a headache, when initially participating in the interest-attention feedback loop 300 and experiencing the dual experience 200. Therefore, in one embodiment, a training protocol includes a series of training sessions for the person. Each training session includes the continued execution of the interest-attention feedback loop 300 for gradually extending periods of time. As the person progresses through the training protocol, the person requires a shorter amount of time to suppress binocular fusion, including binocular rivalry, and achieve the dual experience 200 of simultaneously rendering separate left and right mental displays. Further progress through the training protocol may allow the person to enter the dual experience 200 at will.

In summary, embodiments of the interest-attention feedback loop 300 provide the person with a tool to facilitate the simultaneous rendering of separate left mental display 230 and right mental display 240 through the dual experience 200 rather than render one coherent three-dimensional image 130 through binocular fusion 100. Embodiments of the interest-attention feedback loop 300 may also provide more advanced capabilities, such as allowing the person to synthesize novel merging of information presented in two separate images without the fatigue encountered in rapidly switching between sequential images, or to train an operator to process attention and warning signals at the human reflex level and then automatically switching back to binocular fusion 100 and rendering one coherent three-dimensional display 130 when interest in specific signals that surpass an attention threshold are present.

Figure 4:
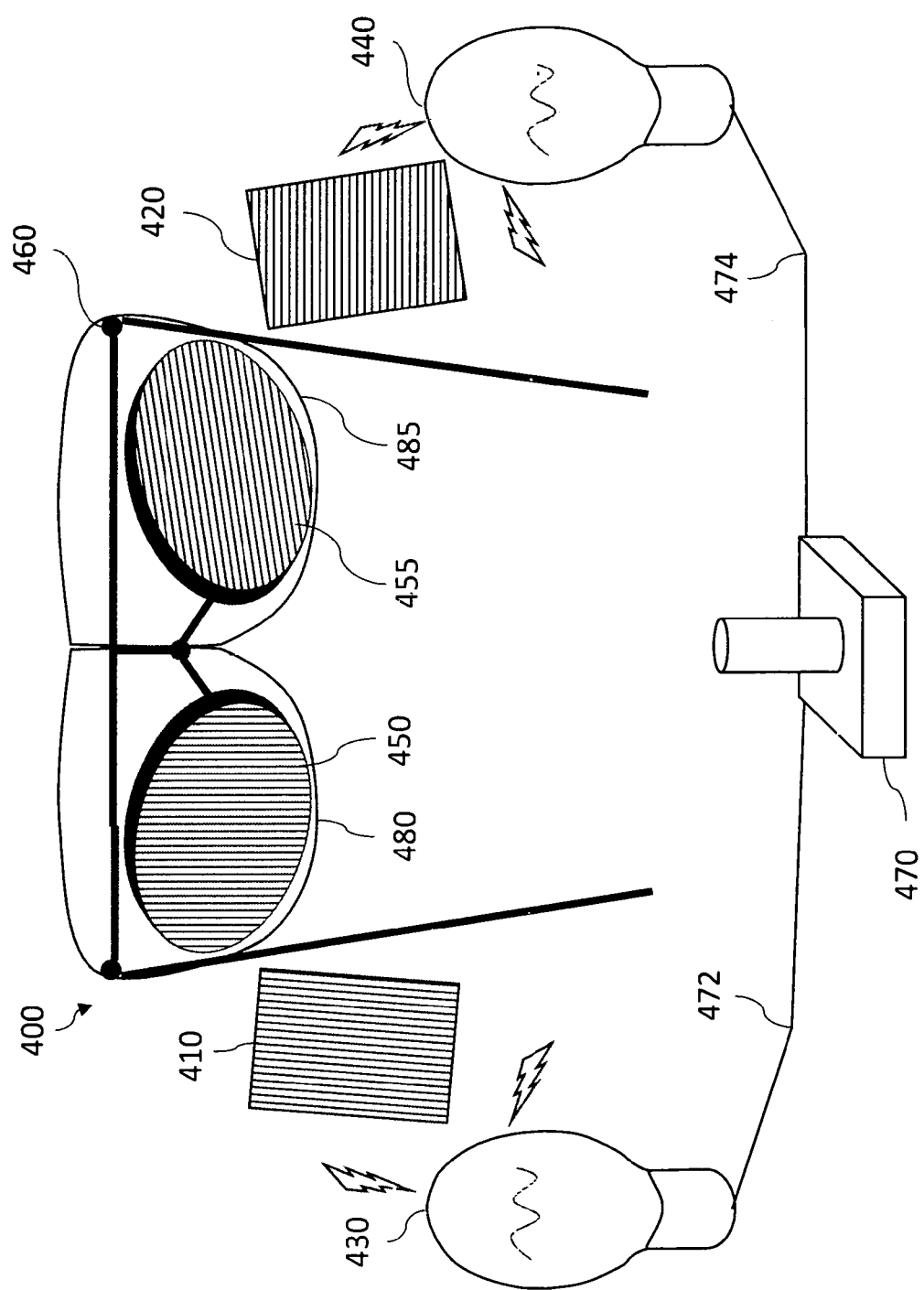
FIG. 4 shows one embodiment of a system to illuminate the left image and the right image with the intensity of two light bulbs controlled by an Illumination intensity controller and two mirrors for reflecting the left image into the left eye of a person and the right image into the right eye of a person.

FIG. 4 shows one embodiment of a system to illuminate the left image 210 and the right image 220 with the intensity of two light bulbs controlled by an Illumination intensity controller and two mirrors for reflecting the left image 210 into the left eye of a person and the right image 220 into the right eye of a person. As shown, the system 400 includes:

Left picture 410.

Right picture 420.

Left light 430 set to shine light at the left picture 410 so as to project the left image 210 from the left picture 410.

Right light 440 set to shine light at the right picture 420 so as to project a right image 220 from the right picture 420.

Illumination intensity controller 470 that is coupled to the left light 430 by interface 472 and coupled to the right light 440 by interface 474. The illumination intensity controller may include a potentiometer that controls the light intensity emitted by the left light 430 and right light 440. In one embodiment, the illumination intensity controller 470 can increase the light intensity emitted by the left light 430 while decreasing the light intensity emitted by the right light 440 and vis-versa.

Left mirror 450 adjusted to reflect the left image 210 from the left picture 410 into the left eye of the person. The left mirror 450 should be shaped in an oval and sized according to the eye socket of the person, so that the left mirror 450 can fit against the nose of the person and encompass, or nearly encompass, the field of view of the person. That is block, as much as possible, the left eye of the person from being able to see anything beyond the left mirror 450.

Right mirror 455 adjusted to reflect the right image 220 from the right picture 420 into the left eye of the person. The right mirror 455 should be shaped in an oval and sized according to the eye socket of the person, so that the right mirror 455 can fit against the nose of the person and encompass, or nearly encompass, the field of view of the person. That is block, as much as possible, the right eye of the person from being able to see anything beyond the right mirror 455.

The left mirror 450 and right mirror 455 should be offset from each other at an angle, e.g. 90 degrees, so as to properly reflect the left image 210 from the left picture 410 into the left eye of the person and the right image 220 from the right picture 420 into the right eye of the person.

Frame 460 holds the left mirror 450 and right mirror 455 and can either be attached to a table mounted stand that the person holds his or her head against or alternatively incorporated into a headband or helmet that is worn on the head of the person. The frame 460, left mirror 450, and right mirror 455 are configured to mitigate or block attention factors in the environment surrounding the person, including attention factors from the frame 460 itself.

Left shade 480 attached to the frame 460 and proximate to the left mirror 450. Left shade 480 blocks the left eye of the person from being able to see anything beyond the left shade 480, including light or objects from the surrounding environment, but not the left mirror 450 or left image 210.

Right shade 485 attached to the frame 460 and proximate to the right mirror 455. Right shade 485 blocks the right eye of the person from being able to see anything beyond the right shade 485, including light or objects from the surrounding environment, but not the right mirror 455 or right image 220.

The system 400 thus executes the interest-attention feedback loop 300 by adjusting the attention factor of image brightness in the left sensor stimulation stream 215 and the attention factor of image brightness in the right sensor stimulation stream 225.

As described, the system 400 presents the left image 210 to the left eye and right image 220 to the right eye at various intensities. The left light 430 shines light at the left picture 410 to project the left image 210 to the left mirror 450, where the left image 210 is then reflected into the left eye of the person as the left sensor stimulation stream 215. Simultaneously, the right light 440 shines light at the right picture 420 to project the right image 220 to the right mirror 455, where the right image 220 is then reflected into the right eye of the person as the right sensor stimulation stream 225.

System 400 implements a voluntary measurement of interest, where the person is required to determine his or her interest in the resulting left sensor stimulation stream 215 and right sensor stimulation stream 225, and then determine adjustments to the attention factors, and adjust the attention factors through some external voluntary muscle action that manipulate the illumination intensity controller 470.

In one embodiment, the hand of the person is used to manipulate the illumination intensity controller 470. The person uses the illumination intensity controller 470 to adjust the brightness of the left image 210 by controlling the light intensity emitted by the left light 430 while also adjusting the brightness of the right image 220 by controlling the light intensity emitted by the right light 440. The adjustments to the brightness of the left image 210 and the brightness of the right image 220 are voluntary adjustments to the attention factor of image brightness within the left sensor stimulation stream 215 and right sensor stimulation stream 225.

The person will typically notice his or her interest shift between the left sensor stimulation stream 215 and right sensor stimulation stream 225. The system 400 implements the interest-attention feedback loop 300 to facilitate the person in balancing this shifting of interest, which will suppress binocular fusion 100 and facilitate the dual experience 200. Training protocols include series of sessions where the person attempts to use system 400 to maintain the dual experience 200 for increasing periods of time.

If the person becomes distracted by attention factors in the environment surrounding the person, then the dual experience 200 may not be achieved. As such, the left mirror 450, right mirror 455, left shade 480, and right shade 485 are described above as positioned to block the environment surrounding the person. In addition, in one embodiment, the system 400 may be used in a darkened room.

In other embodiments, the left mirror 450 and right mirror 455 may be offset from each other at angles less than or greater than 90 degrees, so as to properly reflect the left image 210 into the left eye of the person and the right image 220 into the right eye of the person.

In other embodiments, the illumination intensity controller 470 could be joystick, physical lever, or other mechanism that controls the light intensity emitted by the left light 430 and right light 440. In these alternative embodiments, the person could manipulate the illumination intensity controller 470 with a foot, finger, head, or other body part. In still other embodiments, the left light 430 and right light 440 could be replaced with a single light that can be repositioned by the illumination intensity controller 470 to change the amount of light intensity shining at the left picture 410 and right picture 420.

In other embodiments, one or more of left picture 410, left light 430, right picture 420, and right light 440 could be replaced by other mechanism for projecting the left image 210 at the left mirror 450 and right image 220 at the right mirror 455, such as one or more moving objects or one or more digital displays.

Figure 5:
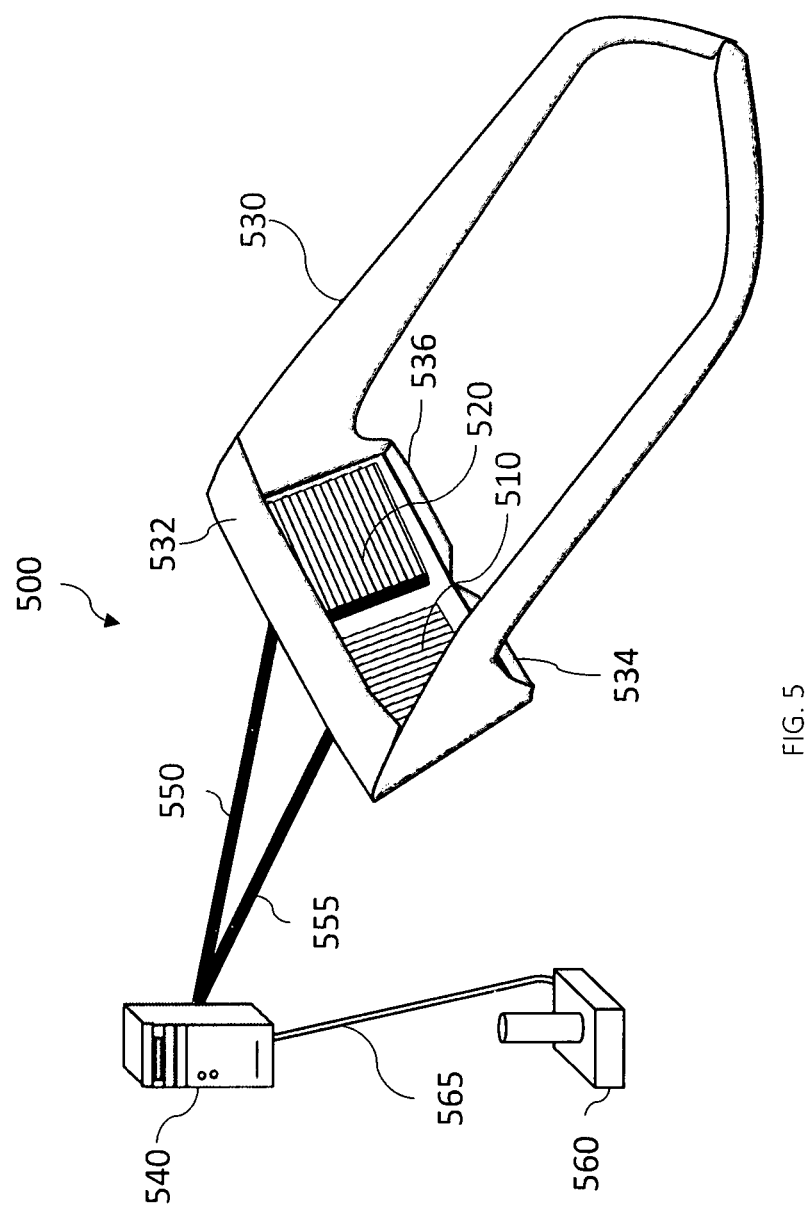
FIG. 5 shows one embodiment of a system using a computer to generate the left image and the right image that are presented on screens mounted in front of the left and right eye of a person.

FIG. 5 shows one embodiment of a system using a computer to generate the left image 210 and the right image 220 that are presented on screens mounted in front of the left and right eye of a person. As shown, the system 500 includes:

Right screen 520 coupled to the computer 540 by an interface 550 that presents the left image 210 to the left eye of the person as the left sensor stimulation stream 215.

Left screen 510 coupled to the computer 540 by an interface 555 and presents the right image 220 to the right eye of the person as the right sensor stimulation stream 225.

A frame 530 that holds the right screen 532 and left screen 534 and includes top shade 532, left shade 534, and right shade 536. The frame 530 can either be attached to a table mounted stand that the person holds his or her head against or alternatively integrated into a headband or helmet that is worn on the head of the person. The top shade 532, left shade 534, and right shade 536 are shaped to the contour of a human face, so as to blocks the eyes of the person from being able to see anything beyond the right screen 520 and left screen 510, including light or objects from the surrounding environment or the frame 530 itself.

Computer 540 includes one or more microprocessors and memory.

Feedback controller 560 that is coupled to the computer 540 by the interface 565. The feedback controller 560 is manipulated by the person to determine his or her interest in the left sensor stimulation stream 215 and right sensor stimulation stream 225, similarly to the illumination intensity controller 470 in system 400. However, in system 500, the person reports his or her interest in the left sensor stimulation stream 215 and right sensor stimulation stream 225 by manipulating the feedback controller 560. Instructions stored as one or more programs in the memory of the computer 540 are executed by the one or more microprocessors of the computer 540 to repeatedly monitor the state of the feedback controller 560 to determine the interest of the person in the separate left sensor stimulation stream 215 and right sensor stimulation stream 225, determine adjustments to the attention factors based on the interest of the person in the left sensor stimulation stream 215 and right sensor stimulation stream 225, and apply the adjustments the attention factors in left sensor stimulation stream 215 and right sensor stimulation stream 225.

The one or more programs in computer 540 also include instructions to apply the adjustments to the attention factors in left sensor stimulation stream 215 and right sensor stimulation stream 225 by modifying the left image 210 and right image 220, transferring the left image 210 to the left screen 510 via interface 555, and transferring the right image 220 to the right screen 520 via interface 550.

The one or more programs executed by the computer 540 include instructions to adjust the attention factors in the left sensor stimulation stream 215 and right sensor stimulation stream 225 according to the interest-attention feedback loop 300 to facilitate, or train, the person to operate within the dual experience 200. As discussed, the one or more programs do not include instructions to perform medical corrective procedures of faulty binocular fusion, as found in the prior art.

System 500 implements a voluntary measurement of interest, where the system 500 determines the interest of the person in the separate left sensor stimulation stream 215 and right sensor stimulation stream 225 based on the voluntary actions of the person in controlling the position of the feedback controller 560.

In other embodiments, the computer 540 could be one or more computers, mobile devices, smart phones, or another suitable electronic device for generating a left image and right image. In still other embodiments, the computer 540 and/or the Illumination intensity controller 560 may be integrated into the frame 530 or into each other.

Figure 6:
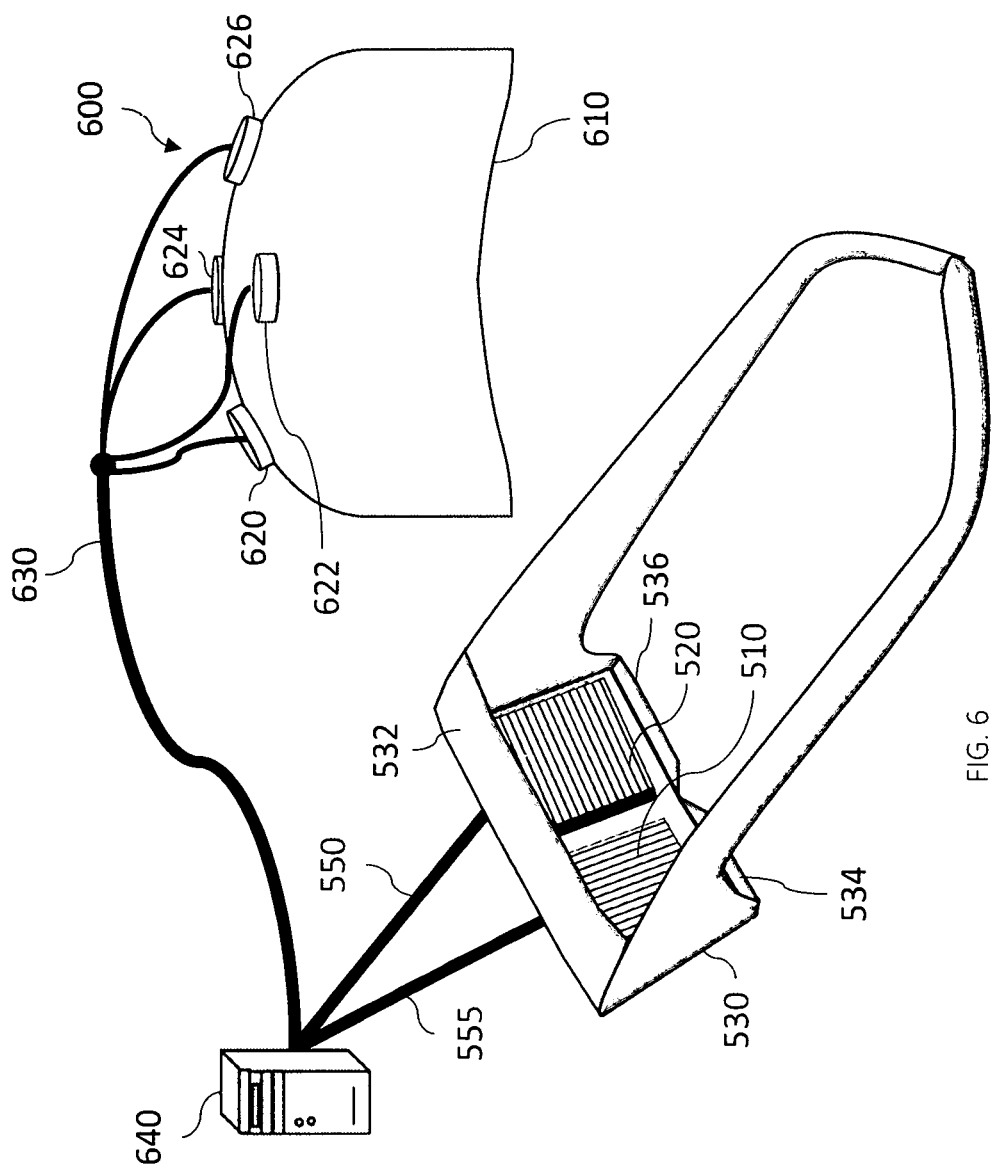
FIG. 6 shows one embodiment of a system that includes electro-encephalogram ("EEG") scalp mounted electrodes to measure the interest of a person in the left sensor stimulation stream 215 and right sensor stimulation stream 225.

FIG. 6 shows one embodiment of a system 600 that includes electro-encephalogram ("EEG") scalp mounted electrodes to measure the interest of a person in left sensor stimulation stream 215 and right sensor stimulation stream 225. As shown, the system 600 includes:

The right screen 520, left screen 510, interface 550, interface 555, frame 530, top shade 532, left shade 534, and right shade 536 are from system 500.

A plurality of EEG electrodes 620, 622, 624, and 626 that are coupled to the computer 640 by the interface 630 and held against the scalp of the person by the EEG mount 610.

Embodiments such as system 600 operate similarly to embodiment such as system 500, where a computer 640 executes the one or more programs to adjust the attention factors in the left sensor stimulation stream 215 and right sensor stimulation stream 225 to facilitate, or train, the person to operate within the dual experience 200. However, system 600 implements an involuntary measurement of interest, where EEG electrodes 620, 622, 624, and 626 are used to determine the interest of the person in the left sensor stimulation stream 215 and right sensor stimulation stream 225. The EEG electrodes 620, 622, 624, and 626 are placed on the scalp of the person and detect electrical activity, or EEG signals, in the brain of the person. Instructions stored as one or more programs in the memory of the computer 640 are executed by the one or more microprocessors of the computer 640 to repeatedly monitor and interpret the signals received from the EEG electrodes 620, 622, 624, and 626 via the interface 630. The one or more programs also include instructions to interpret the signals received from the EEG electrodes 620, 622, 624, and 626 into data representing a measurement of the interest of the person in the separate left and right sensor stimulation streams. As such, the one or more programs that include instructions to interpret the signals received from the EEG electrodes 620, 622, 624, and 626 and the EEG electrodes 620, 622, 624, and 626, form a feedback controller that determines an involuntary measurement of interest.

The one or more programs executed by computer 640 also include instructions to determine adjustments to the attention factors based on the measurement of the interest of the person in the separate left and right sensor stimulation streams from the EEG electrodes 620, 622, 624, and 626, and apply the adjustments the attention factors in left sensor stimulation stream 215 and right sensor stimulation stream 225. Like computer 540, computer 640 also includes programs with instructions to apply the adjustments to the attention factors in left sensor stimulation stream 215 and right sensor stimulation stream 225 by modifying the left image 210 and right image 220, transferring the left image 210 to the left screen 510 via interface 555, and transferring the right image 220 to the right screen 520 via interface 550.

As described, the operation of embodiments such as system 600 is different than embodiments such as system 400 or 500. The determination of the interest of the person in the left sensor stimulation stream 215 and right sensor stimulation stream 225 is performed by the system 600 based on measuring the state of the person, thus relieving the person the task of manually performing some voluntary actions. Without having to perform such actions, the person may be able to better focus on selecting and interacting with data from either the left image 210 or right image 220 and performing manual operations in response to the data.

Further, embodiments such as system 600 may execute the interest-attention feedback loop 300 more quickly than system 400 or 500, which may better facilitate the person to operate within the dual experience 200.

EEG electrodes and programs to monitor the signals from the EEG electrodes are commercially available and known in the prior art. One skilled in the arts could implement a computer 640 that includes one or more programs to monitor and interpret the signals from the EEG electrodes 620, 622, 624, and 626. However, utilization of such technology in an interest-attention feedback loop 300 or to facilitate the dual experience 200 is not known in the prior art.

In other embodiments the plurality of EEG electrodes 620, 622, 624, and 626 could be any reasonable number of EEG.

Furthermore, one skilled in the arts can realize EEG electrodes are not the only sensors that may be used to measure the interest of the person in the left sensor stimulation stream 215 and right sensor stimulation stream 225. Other embodiments could include other sensors and accompanying programs in the computer 640 to form a feedback controller that measures the interest of a person in the left sensor stimulation stream 215 and right sensor stimulation stream 225, such as sensors for eye tracking, pupil dilation, and facial expressions.

In other embodiments, the computer 640 could be one or more computers, mobile devices, smart phones, or other suitable electronic device for generating a left image and right image. In still other embodiments, the computer 640 may be integrated into the frame 530 and/or the frame 530 may also be integrated with the EEG mount 610 and hold the EEG electrodes 620, 622, 624, and 626.

Figure 7:
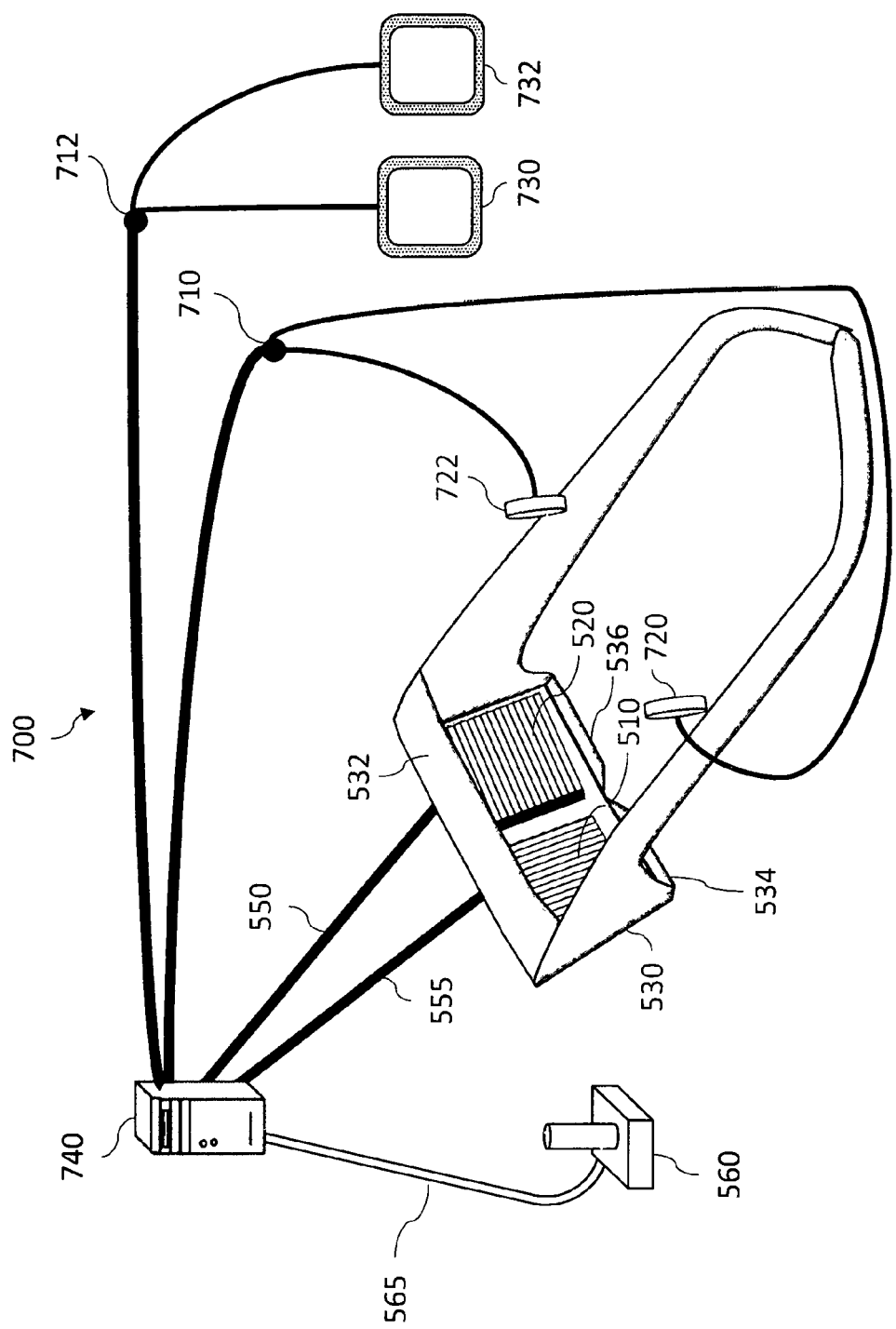
FIG. 7 shows one embodiment of a system with separate left and right audio generators to be placed over the left and right ear and tactile patches to be placed on the left and right body to present additional inputs to the left sensor stimulation stream and right sensor stimulation stream.

FIG. 7 shows one embodiment of a system with separate left and right audio generators to be placed over the left and right ear and tactile patches to be placed on the left and right side of the body of a person to present additional inputs to the left sensor stimulation stream and right sensor stimulation stream.

The right screen 520, left screen 510, interface 550, interface 555, frame 530, top shade 532, left shade 534, and right shade 536, feedback controller 560, interface 565 are from system 500

Left tactile generator 730 is attached to skin surface on the left side of the person. A small patch is shown, but larger patches with larger coverage area can be used in other embodiments. The left tactile generator 730 is capable of generating tactile stimulations, such as various vibrations or temperatures.

Right tactile generator 732 is attached to skin surface on the right side of the person. A small patch is shown, but larger patches with larger coverage area can be used in other embodiments. The right tactile generator 732 is capable of generating tactile stimulations, such as various vibrations or temperatures.

Left audio generator 720 is placed proximate to the left ear of the person to transmit sound to the left ear of the person. The left audio generator 720 could include baffles to reduce outside noise.

Right audio generator 722 is placed proximate to the right ear of the person to transmit sound to the right ear of the person. The right audio generator 722 could include baffles to reduce outside noise.

Embodiments such as system 700 operate similarly to embodiment such as system 500, where a computer 740 executes the one or more programs to adjust the attention factors in the left sensor stimulation stream 215 and right sensor stimulation stream 225 to facilitate, or train, the person to operate within the dual experience 200.

Similar to the computer 540, the computer 740 includes one or more programs that calculate and apply adjustment to the attention factors in the left sensor stimulation stream 215 and right sensor stimulation stream 225 based on the interest of the person in the left sensor stimulation stream 215 and right sensor stimulation stream 225 as determined from the manipulation of the feedback controller 560 by the person. However, the computer 740 also includes one or more programs to determine and apply adjustments to the attention factors in the left sensor stimulation stream 215 and right sensor stimulation stream 225 by manipulating the tactile sensations produced by the left tactile generator 730 and right tactile generator 732 and the sound produced by the left audio generator 720 and right audio generator 722.

In one embodiment, the one or more programs may adjust the adjust the attention factors in the left sensor stimulation stream 215 and right sensor stimulation stream 225 by increasing or decreasing the volume of the sound produced by the left audio generator 720 and right audio generator 722. In some embodiments manipulations of the left image 210 and right image 220 may correspond to changes in the sound produced adjustments by the left audio generator 720 and right audio generator 722.

Though only a single feedback controller 560 is shown in system 700, in other embodiments additional controllers can be added and assigned to determine the visual, audio, or tactile attention factors of the left sensor stimulation stream 215 and right sensor stimulation stream 225.

In still other embodiments, the left audio generator 720, the right audio generator 722, the left tactile generator 730, and/or the right tactile generator 732 could be combined with the system 400 or the system 600.

We claim:

1. A method for facilitating a dual experience in a person, comprising:
   (a) presenting, by a controller, a left optic stimulation pattern with a left transmitter to encompass a field of view of a left eye of the person, and presenting, by the controller, a right optic stimulation pattern with a right transmitter to encompass a field of view of a right eye of the person, wherein the right optic stimulation pattern is different from the left optic stimulation pattern,
   (b) determining, by the controller based on receiving sensor data from one or more sensors, one or more measurements of a first level of interest of the person in the left optic stimulation pattern and a second level of interest of the person in the right optic stimulation pattern,
   (c) determining, by the controller, one or more adjustments to one or more attention factors of at least one of the left optic stimulation pattern and the right optic stimulation pattern, wherein the controller determines the one or more adjustments based upon the one or more measurements and causing a balancing of the first level of interest and the second level of interest of the person,
   (d) applying, by the controller, the one or more adjustments to suppress binocular fusion and binocular rivalry in the person in order to maintain the dual experience in the person, where the person simultaneously renders and has awareness of a left mental display derived from a left optic stimulation pattern and a separate right mental display derived from a right optic stimulation pattern, and
   (e) repeating, by the controller, steps (a)-(e) in real-time.

2. The method of claim 1, wherein the one or more attention factors of at least one of the left optic stimulation pattern and the right optic stimulation pattern comprise at least one of:
   color,
   illumination,
   or image movement.

3. The method of claim 1, wherein determining the first level of interest and the second level of interest includes measuring, with the one or more sensors, at least one movement of the person.

4. The method of claim 1, wherein the one or more sensors and the controller are included in a single lever mechanism.

5. The method of claim 1, wherein determining and applying the one or more adjustments to the one or more attention factors of the left optic stimulation pattern further comprises outputting, by the controller via a left audio generator proximate to the left ear of the person, a left auditory stimulations pattern, and wherein determining and applying the one or more adjustments to the one or more attention factors of the right optic stimulation pattern further comprises outputting, by the controller via a right audio generator proximate to the right ear of the person, a right auditory stimulation pattern.

6. The method of claim 1, wherein determining, by the controller, the one or more adjustments further comprises determining, by the controller, one or more adjustments to counteract one or more intrinsic alterations of at least one of the left optic stimulation pattern and the right optic stimulation pattern, wherein the one or more intrinsic alterations would otherwise influence the person to not balance the first level of interest and the second level of interest.

7. The method of claim 1, where determining the first level of interest and the second level of interest includes measuring involuntary changes in the person with the one or more sensors.

8. The method of claim 1, wherein the left transmitter further comprises a left mirror positioned at an angle to the left eye of the person that reflects the left optic stimulation pattern presented by the left transmitter to the left eye of the person, and wherein the right transmitter further comprises a right mirror positioned at an angle to the right eye of the person that reflects the right optic stimulation pattern presented by the right transmitter to the right eye of the person.

9. The method of claim 8, wherein:
the left mirror is positioned proximate to the face of the person to reflect the left optic stimulation pattern to the field of view of the left eye of the person, and
the right mirror is positioned proximate to the face of the person to reflect the right optic stimulation pattern to the field of view of the right eye of the person.

10. The method of claim 9, wherein:
the left mirror is coupled with one or more left opaque surfaces that prevent optical signals from an environment proximate to the person from entering the left eye; and
the right mirror is coupled with one or more right opaque surfaces that prevent optical signals from the environment proximate to the person from entering the right eye.

11. A device to facilitate a dual experience in a person, comprising:
a left screen positioned proximate to a left eye of a person, so as to encompass a field of view of the left eye of the person,
a right screen positioned proximate to a right eye of the person, so as to encompass a field of view of the right eye of the person,
one or more sensors, and
a computer coupled to the left screen, the right screen, and the one or more sensors, which includes a non-transitory computer readable medium and a microprocessor configured to execute instructions for presenting a left optic stimulation pattern and a right optic stimulation pattern, wherein the executed instructions cause the computer to perform operations comprising:
(a) displaying, by the computer, the left optic stimulation pattern on the left screen and displaying, by the computer, a right optic stimulation pattern on the right screen, wherein the left optic stimulation pattern is different from the right optic stimulation pattern,
(b) determining, by the computer based on receiving sensor data from the one or more sensors, one or more measurements of a first level of interest of the person in the left optic stimulation pattern and a second level of interest of the person in the right optic stimulation pattern,
(c) determining, by the computer, one or more adjustments to one or more attention factors of at least one of the left optic stimulation pattern and the right optic stimulation pattern, wherein the computer determines the one or more adjustments based upon the one or more measurements and causing a balancing of the first level of interest and the second level of interest,
(d) applying, by the computer, the one or more adjustments to suppress binocular fusion and binocular rivalry in the person in order to maintain the dual experience in the person, where the person simultaneously renders and has awareness of a left mental display derived from a left optic stimulation pattern and a separate right mental display derived from a right optic stimulation pattern, and
(e) repeating, by the computer, steps (a)-(e) in real-time.

12. The device of claim 11, wherein:
the left screen is positioned at an angle to the left eye of the person to display the left optic stimulation pattern to the majority of the field of view of the left eye, and
the right screen is positioned at an angle to the right eye of the person to display the right optic stimulation pattern to the majority of the field of view of the right eye.

13. The device of claim 12, wherein:
the left screen is coupled with one or more left opaque surfaces that prevents optical signals from an environment in-front the person from entering the left eye, and
the right screen is coupled with one or more right opaque surfaces that prevents optical signals from the environment in-front of the person from entering the right eye.

14. The device of claim 13, wherein:
the one or more left opaque surfaces are composed of a blackened featureless material to prevent the person from directing attention away from the left screen, and
the one or more right opaque surfaces are composed of a blackened featureless material to prevent the person from directing attention away from the right screen.

* * * * *